(12) United States Patent
Schultz

(10) Patent No.: US 9,977,871 B2
(45) Date of Patent: May 22, 2018

(54) CASSETTE CONTROL INCLUDING PRESENCE SENSING AND VERIFICATION

(71) Applicant: Kirby Lester, LLC, Lake Forest, IL (US)

(72) Inventor: David A. Schultz, Palatine, IL (US)

(73) Assignee: Capsa Solutions LLC, Portland, OR (US)

( * ) Notice: Subject to any disclaimer, the term of this patent is extended or adjusted under 35 U.S.C. 154(b) by 327 days.

(21) Appl. No.: 14/155,073

(22) Filed: Jan. 14, 2014

(65) Prior Publication Data

US 2015/0196458 A1 Jul. 16, 2015

(51) Int. Cl.
*A61J 7/00* (2006.01)
*G06F 19/00* (2018.01)
*G07F 17/00* (2006.01)

(52) U.S. Cl.
CPC ...... *G06F 19/3462* (2013.01); *G07F 17/0092* (2013.01)

(58) Field of Classification Search
USPC ......................................................... 700/236
See application file for complete search history.

(56) References Cited

U.S. PATENT DOCUMENTS

| | | |
|---|---|---|
| 3,789,194 A | 1/1974 | Kirby |
| 4,847,764 A | 7/1989 | Halvorson |
| 4,901,841 A | 2/1990 | Haggerty et al. |
| 4,903,861 A | 2/1990 | Yuyama |
| 5,027,938 A | 7/1991 | Haggarty et al. |
| 5,208,762 A | 5/1993 | Charhut et al. |
| 5,317,645 A | 5/1994 | Perozek et al. |
| 5,337,919 A | 8/1994 | Spaulding et al. |
| 5,473,703 A | 12/1995 | Smith |
| 5,597,995 A | 1/1997 | Williams et al. |
| 5,666,492 A | 9/1997 | Rhodes et al. |

(Continued)

OTHER PUBLICATIONS

KL16 Operating Instructions, Kirby Lester LLC, Stamford, CT. Date: 2006.

(Continued)

*Primary Examiner* — Gene O Crawford
*Assistant Examiner* — Stephen L Akridge
(74) *Attorney, Agent, or Firm* — Jansson Munger McKinley & Kirby Ltd.

(57) ABSTRACT

A method for controlling medicament dispensing from a cassette moved from a mount for the cassette includes mounting the cassette fully on the mount, the cassette being loaded with bulk-form medicaments, generating a first signal indicating that the cassette is fully mounted, enabling operation of the cassette responsive to the first signal, unmounting the cassette at least partially from the mount, generating a second signal indicating that the cassette has been at least partially unmounted, and disabling further operation of the cassette responsive to the second signal even if the cassette is fully remounted. The method may include also generating a third signal indicating that the cassette is ready for further dispensing of medicaments, remounting the cassette fully on the mount, generating the first signal indicating that the cassette is fully remounted, and enabling further operation of the cassette responsive to the first and third signals after disabling further operation of the cassette.

25 Claims, 9 Drawing Sheets

(56) References Cited

U.S. PATENT DOCUMENTS

| | | | |
|---|---|---|---|
| 5,713,485 A | 2/1998 | Liff et al. | |
| 5,713,487 A | 2/1998 | Coughlin | |
| 5,737,539 A | 4/1998 | Edelson et al. | |
| 5,758,095 A | 5/1998 | Albaum et al. | |
| 5,761,877 A | 6/1998 | Quandt | |
| 5,762,235 A * | 6/1998 | Coughlin | G06Q 20/342 221/131 |
| 5,768,327 A | 6/1998 | Pinto et al. | |
| 5,797,515 A | 8/1998 | Liff et al. | |
| 5,845,255 A | 12/1998 | Mayaud | |
| 5,883,370 A | 3/1999 | Walker et al. | |
| 5,907,493 A | 5/1999 | Boyer et al. | |
| 5,988,858 A | 11/1999 | Yuyama et al. | |
| 5,993,046 A | 11/1999 | McGrady et al. | |
| 6,021,392 A | 2/2000 | Lester et al. | |
| 6,036,812 A | 3/2000 | Williams et al. | |
| 6,068,156 A | 5/2000 | Liff et al. | |
| 6,112,182 A | 8/2000 | Akers et al. | |
| 6,152,364 A | 11/2000 | Schoonen et al. | |
| 6,170,230 B1 | 1/2001 | Chudy et al. | |
| 6,202,923 B1 | 3/2001 | Boyer et al. | |
| 6,219,587 B1 | 4/2001 | Ahlin et al. | |
| 6,230,927 B1 * | 5/2001 | Schoonen | A61J 7/0084 221/10 |
| 6,256,967 B1 | 7/2001 | Hebron et al. | |
| 6,283,322 B1 | 9/2001 | Liff et al. | |
| 6,317,648 B1 | 11/2001 | Sleep et al. | |
| 6,330,491 B1 | 12/2001 | Lion | |
| 6,351,688 B1 | 2/2002 | Nichols et al. | |
| 6,352,200 B1 | 3/2002 | Schoonen et al. | |
| 6,370,841 B1 * | 4/2002 | Chudy | B65B 5/103 221/10 |
| 6,421,584 B1 | 7/2002 | Norberg et al. | |
| 6,438,451 B1 | 8/2002 | Lion | |
| RE37,829 E | 9/2002 | Charhut et al. | |
| 6,529,801 B1 | 3/2003 | Rosenblum | |
| 6,554,157 B2 | 4/2003 | Geltser et al. | |
| 6,684,914 B2 | 2/2004 | Gershman et al. | |
| 6,702,146 B2 | 3/2004 | Varis | |
| 6,775,589 B2 | 8/2004 | William et al. | |
| 7,124,791 B2 | 10/2006 | Geltser et al. | |
| 7,263,411 B2 * | 8/2007 | Shows | G06F 19/3462 221/2 |
| 7,349,858 B1 | 3/2008 | McGrady et al. | |
| 7,395,841 B2 | 7/2008 | Geltser et al. | |
| 7,395,946 B2 | 7/2008 | Yuyama et al. | |
| 7,434,704 B2 | 10/2008 | Yuyama et al. | |
| 7,963,201 B2 * | 6/2011 | Willoughby | A61J 7/0084 117/106 |
| 8,271,128 B1 * | 9/2012 | Schultz | A61J 7/02 700/236 |
| 2001/0002448 A1 | 5/2001 | Wilson et al. | |
| 2002/0032582 A1 | 3/2002 | Feeney, Jr. et al. | |
| 2002/0062175 A1 | 5/2002 | Lion | |
| 2003/0057230 A1 | 3/2003 | Stevens et al. | |
| 2003/0225595 A1 | 12/2003 | Helmus et al. | |
| 2004/0088187 A1 | 5/2004 | Chudy et al. | |
| 2004/0107022 A1 | 6/2004 | Gomez | |
| 2005/0125097 A1 * | 6/2005 | Chudy | G06F 19/3462 700/236 |
| 2006/0058724 A1 * | 3/2006 | Handfield | A61J 7/0084 604/20 |
| 2006/0253346 A1 | 11/2006 | Gomez | |
| 2007/0116792 A1 * | 5/2007 | Yuyama | G07F 11/44 425/193 |
| 2007/0173971 A1 | 7/2007 | Richardson et al. | |
| 2008/0011764 A1 | 1/2008 | Geltser et al. | |
| 2008/0029530 A1 | 2/2008 | Yuyama et al. | |
| 2010/0287880 A1 * | 11/2010 | Yasunaga | A61J 7/0084 53/64 |

OTHER PUBLICATIONS

Yuyama Adding New Medications product information, <www.yuyamarx.com>, Yuyama USA, Inc., Elk Grove Village, IL. Date: 2008.

Yuyama EV-120 product brochure, Yuyama USA, Inc., Elk Grove Village, IL. Undated.

Yuyama EV-220 product brochure, Yuyama USA, Inc., Elk Grove Village, IL. Undated.

Yuyama Vial Filling Technology product information, <www.yuyamarx.com>, Yuyama USA, Inc., Elk Grove Village, IL. Date: 2008.

Vial Filing Systems: EV-54 Date: 2008.
Tablet Packaging Systems: FDS-II PROUD, Date: 2008.
Tablet Packaging Machines, Date: 2008.

* cited by examiner

CASSETTE CONTROL INCLUDING PRESENCE SENSING AND VERIFICATION

FIELD

The field relates generally to workflow management of medicaments and, more particularly, to handling of medicaments in controlled environments.

BACKGROUND

In retail, hospital, long-term-care and mail order medicament dispensing, a large number of different prescription orders must be fulfilled. The prescription orders may include one or more prescription for single-dose medications or medicaments, such as tablets. Fulfillment as used herein refers to the process of handling and executing customer orders. The term "tablets" and "medicaments" as used herein should be understood as being generic to tablets, capsules, caplets and any other solid-dose medication types including prescription and non-prescription medications, products and the like.

Automatic vial filling machines, automatic pouch packaging machines and other types of medicament filling machines under control of a data processing platform are used in pharmacy locations to store bulk medicaments in removable storage modules frequently referred to as "cassettes." Periodically, it in necessary to replenish bulk medicaments in the cassettes or return such medicaments to stock in the case of unclaimed medicaments. In order to replenish cassettes or return medicaments to stock, the pharmacy user typically must remove a cassette from a mount and load medicaments into the cassette. With existing machines using cassettes, there is no control or supervision over operation of cassettes that are removed from the machine for loading, or for any other reason. As a result, there is a chance, no matter how small, that incorrect medicaments could be loaded into a cassette.

For example, in a return-to-stock scenario, it may be necessary to return unclaimed medicaments from a pharmacy will-call holding area back to a cassette. As is known, medicaments frequently look alike, yet can have different active ingredients and strengths. Given the look-a-like nature of medicaments, a pharmacy user could inadvertently load a cassette with a medicament that has the same physical appearance as the medicament in the cassette, yet is different in type or strength.

In a replenishment scenario there is also a risk that the wrong medicament could be loaded into a cassette, if the cassette could be simply replenished without any further level of control. For example, a user might replenish a cassette without careful verification because of a perceived need to quickly fill a prescription order. A further example could include a busy pharmacy user who might properly replenish a cassette, yet put the cassette aside to perform other tasks, possibly permitting contamination of the medicaments in the cassette by some agent or other contaminate. It is also possible that the cassette could be accessed by an unauthorized user when set aside. No matter how small the opportunity, errors could occur if the cassette replenishment process is not completed immediately and a partially filled cassette is allowed to sit idle in a busy pharmacy.

Further, with any restocking or replenishment process performed by a human, there is small risk of error. Involvement of and supervision by senior pharmacy personnel in the restocking or replenishing procedure may be useful to reduce such risk of error.

It would be an improvement in the art to provide a system and method which would improve the restocking and replenishment process used in pharmacies including providing for a supervised loading process including restocking and replenishment. Such an improved loading process would provide an increased likelihood that the cassette is restocked or replenished with bulk medicaments in the proper manner and would contribute to the improvement and quality of patient care.

SUMMARY

A method for controlling medicament dispensing from a cassette moved from a mount for the cassette is described herein. In an embodiment, the method includes mounting the cassette fully on the mount. The mounted cassette is preferably loaded with bulk-form medicaments. A first signal is generated indicating that the cassette is fully mounted. Operation of the cassette is enabled responsive to the first signal. Subsequently, the cassette is at least partially unmounted from the mount. Upon full or partial unmounting of the cassette, a second signal is generated. Further operation of the cassette is disabled in response to the second signal even if the cassette is fully remounted thereafter.

The method may also include certain steps occurring after the cassette is disabled. These steps preferably included generating a third signal indicating that the cassette is ready for further dispensing of medicaments. The third signal may be generally responsive to completing a verification process. When the cassette is remounted fully on the mount, the first generated signal indicates that the cassette is fully remounted and enables further operation of the cassette responsive to the first and third signals.

The method for controlling medicament dispensing from a cassette may also include, before or after loading further bulk-form medicaments into the cassette, the step of verifying that the cassette was correctly loaded with the medicaments. Generating the third signal indicating that the cassette is ready for further dispensing of medicaments may also include triggering the third signal with a user-input device. Further, triggering the third signal with the user-input device may include the step of placing a finger against a fingerprint reader user-input device. Triggering the third signal with the user-input device may include the step of placing a finger against a touch screen video display user-input device. In addition, triggering the third signal with the user-input device may also include reading a code associated with the cassette with a code reader user-input device.

The method step of generating the first signal may also include contacting a switch with the cassette when the cassette is fully mounted or fully remounted. The method step of generating the second signal may also include spacing the cassette from the switch when the cassette is at least partially unmounted.

The method for controlling medicament dispensing from a cassette may further include, after enabling operation of the cassette, the step of dispensing medicaments from the cassette. Dispensing medicaments from the cassette may also include the step of dispensing all of the medicaments from the cassette. The method for controlling medicament dispensing from a cassette may also include, after unmounting the cassette at least partially from the mount, the step of loading further bulk-form medicaments into the cassette. In instances where the cassette includes a lid, the method may further include, after unmounting the cassette at least partially from the mount and before loading further bulk-form medicaments into the cassette, the steps of allowing the lid to open when the cassette is at least partially unmounted. The method may also include the step of opening the lid and permitting the medicaments to be loaded into the cassette.

The method for controlling medicament dispensing from a cassette may also include generating the second signal and starting a timer. In addition, a timer may be started after generating the second signal before mounting the cassette fully on the mount.

The method may also include a verification process for verifying correct medicaments selected for loading in a cassette or that the medicaments are identical to other medicaments in the cassette. In the embodiment, a fourth signal may be generated identifying the cassette, and a fifth signal may be generated identifying a container holding a medicament to be loaded into the cassette. A sixth signal may be generated identifying a match of the cassette and the container holding the medicament before enabling further operation of the cassette.

The method may also include providing a container holding an unclaimed prescription with medicaments to be restocked into the cassette. In addition, the method may provide a supply container which holds a quantity of medicaments to be poured into the cassette.

In the embodiments, appropriate logic, software and hardware may be provided to sense the presence of a cassette on its mount and generate signals indicating the presence or absence of the cassette. The combination of the logic, software and hardware such as a micro-switch may provide a signal indicating whether the cassette has been removed since the cassette was last mounted in its operating mode to allow operation and dispensing of medicaments from the cassette. In embodiments, the combination of the logic, software and hardware such as a micro-switch may also sense when the cassette is partially or fully unmounted to disable operation of the cassette to prevent dispensing of medicaments from the cassette. In this mode, the operation of the cassette is also disabled preventing dispensing of medicaments from the cassette until a verification is performed which enables the cassette to further dispense medicaments. Accordingly, when a cassette is fully or partially unmounted, the logic, software and hardware can both notify the operator and require supervision to enable the cassette to become operative to dispense medicaments. In the exemplary embodiment, the micro-switch with appropriate logic and software provides the opportunity for supervision of cassette replenishment and dispensing. The micro-switch is activated if the cassette is removed or returned. If the cassette is removed, even for a very brief moment, the logic and software will receive a signal from the switch, and any further dispensing from the cassette can be supervised, requiring qualifying actions by a pharmacist before dispensing from the cassette can resume.

BRIEF DESCRIPTION OF THE DRAWINGS

Exemplary medicament replenishment systems and methods including controlling medicament dispensing from a cassette may be understood by reference to the following description taken in conjunction with the accompanying drawings, in which like reference numbers identify like elements throughout the different views. The drawings are not necessarily to scale, emphasis instead being placed upon illustrating the principles of the disclosure. In the accompanying drawings.

DETAILED DESCRIPTION

Figure 1:
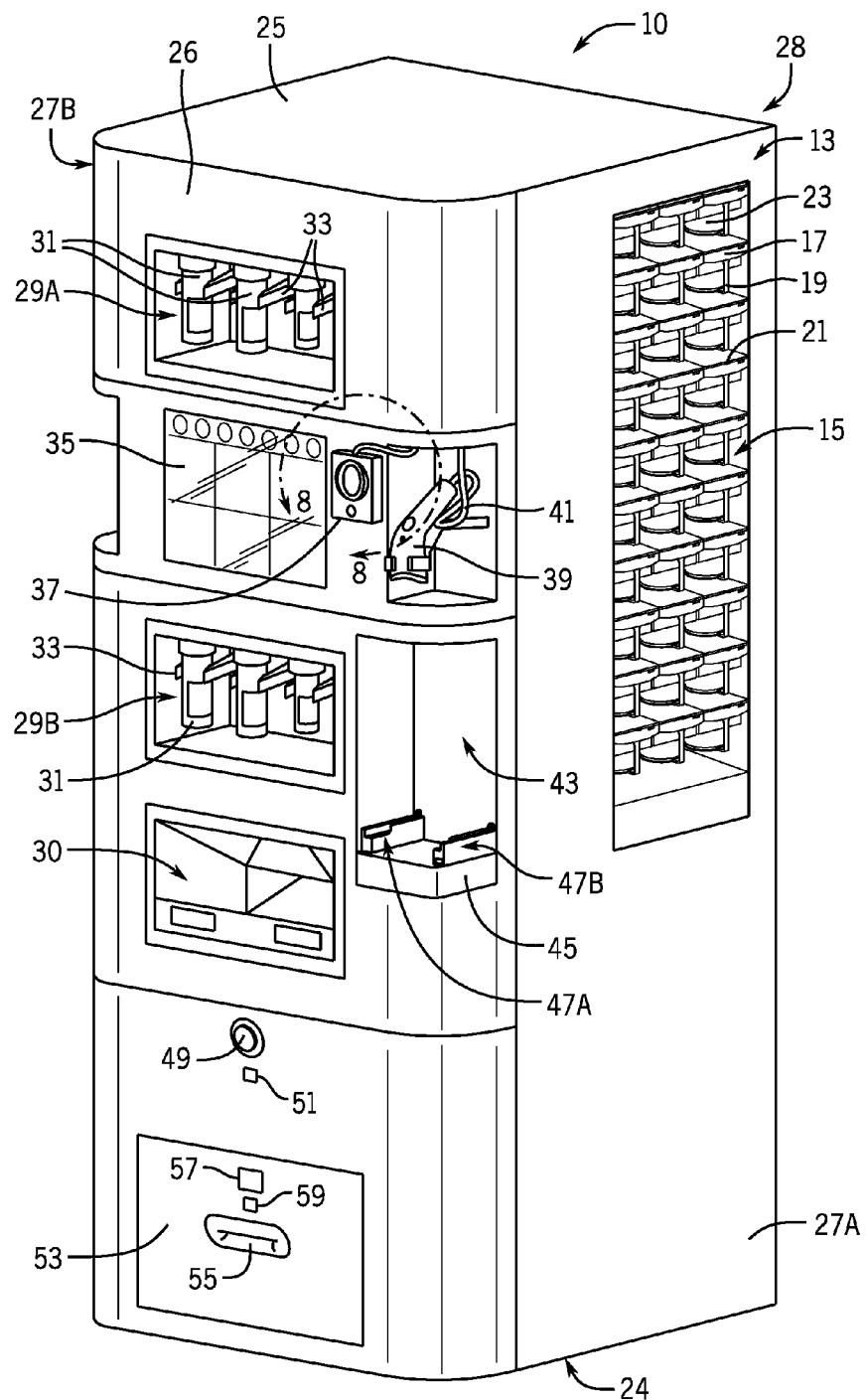
FIG. 1 is a perspective view of an exemplary multi-cassette medicament dispensing machine including an embodiment of the inventive method for controlling medicament dispensing from a cassette.
Figure 2:
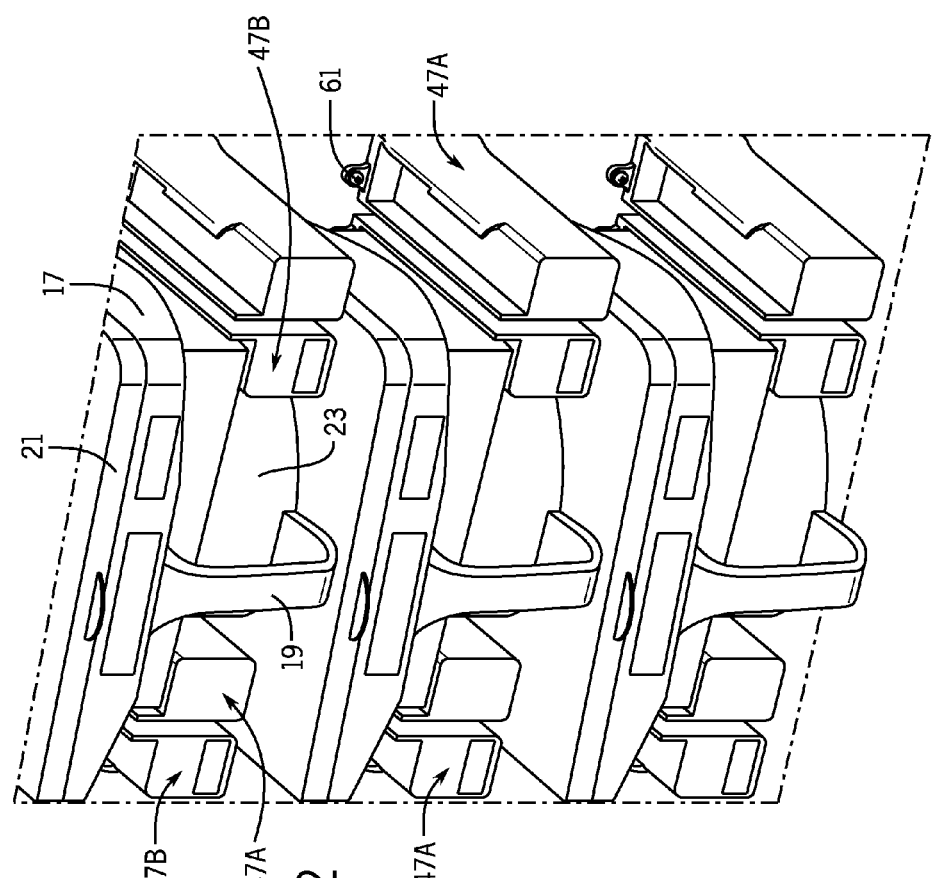
FIG. 2 is an enlarged perspective view of a group of cassettes installed in the multi-cassette medicament dispensing machine of FIG. 1.

Referring first to FIGS. 1-9, an exemplary automatic multi-cassette medicament dispenser 10 including a method for controlling medicament dispensing is illustrated. Multi-cassette medicament dispenser 10 includes a housing 13 that houses a group of cassettes 15 including individual cassettes 17, an automatic tablet counter 93 and a data processing platform 16 (see FIGS. 1 and 10). Data processing platform 16 enables real-time monitoring, polling and data transmission between components of automatic multi-cassette medicament dispenser 10 in response to signals generated during operation of multi-cassette medicament dispenser 10.

As can be seen in FIGS. 1-5, each cassette 17 includes a handle 19, a lid 21 and a base 23. Each cassette may be removed or unmounted from multi-cassette medicament dispensing machine 10 and lid 21 can be raised for refilling or replenishment of medicaments during the typical range of pharmacy work flow tasks. Each cassette may also be partially unmounted from multi-cassette medicament dispensing machine 10 and lid 21 can be raised for loading, replenishment or return to stock operations during pharmacy work flow tasks. The operation of the cassettes 17 are described further below.

The prescription order fulfillment process begins when a prescription order is delivered to the pharmacy. The delivery may be in any suitable manner, including by physically providing a paper prescription order to the pharmacy or by electronic data transmission. The prescription order will include all the information required to fulfill a validated prescription as described herein. The prescription order comprising one or more prescriptions is then entered into multi-cassette medicament dispensing machine 10 by data entry at an input workstation. The data may be input through the use of an input device such as a keyboard, mouse and/or touch-screen video display. Information entered into multi-cassette medicament dispensing machine 10 will typically include patient name, medication type and quantity, physician name, refill information, and may include additional information such as National Drug Code (NDC) for the prescribed medication, medication interaction information and insurance information or other information related to payment. A validated prescription order is transmitted to multi-cassette medicament dispensing machine 10 for dispensing of the medicaments needed to fulfill the validated prescription order.

FIG. 1 illustrates multi-cassette medicament dispensing machine 10 which includes top 25, bottom 24, front 26, side 27A, 27B, and rear 28 housing portions. Multi-cassette medicament dispensing machine 10 preferably stores a plurality of cassettes 15, although the method may be used with one or more cassettes 17.

Figure 10:
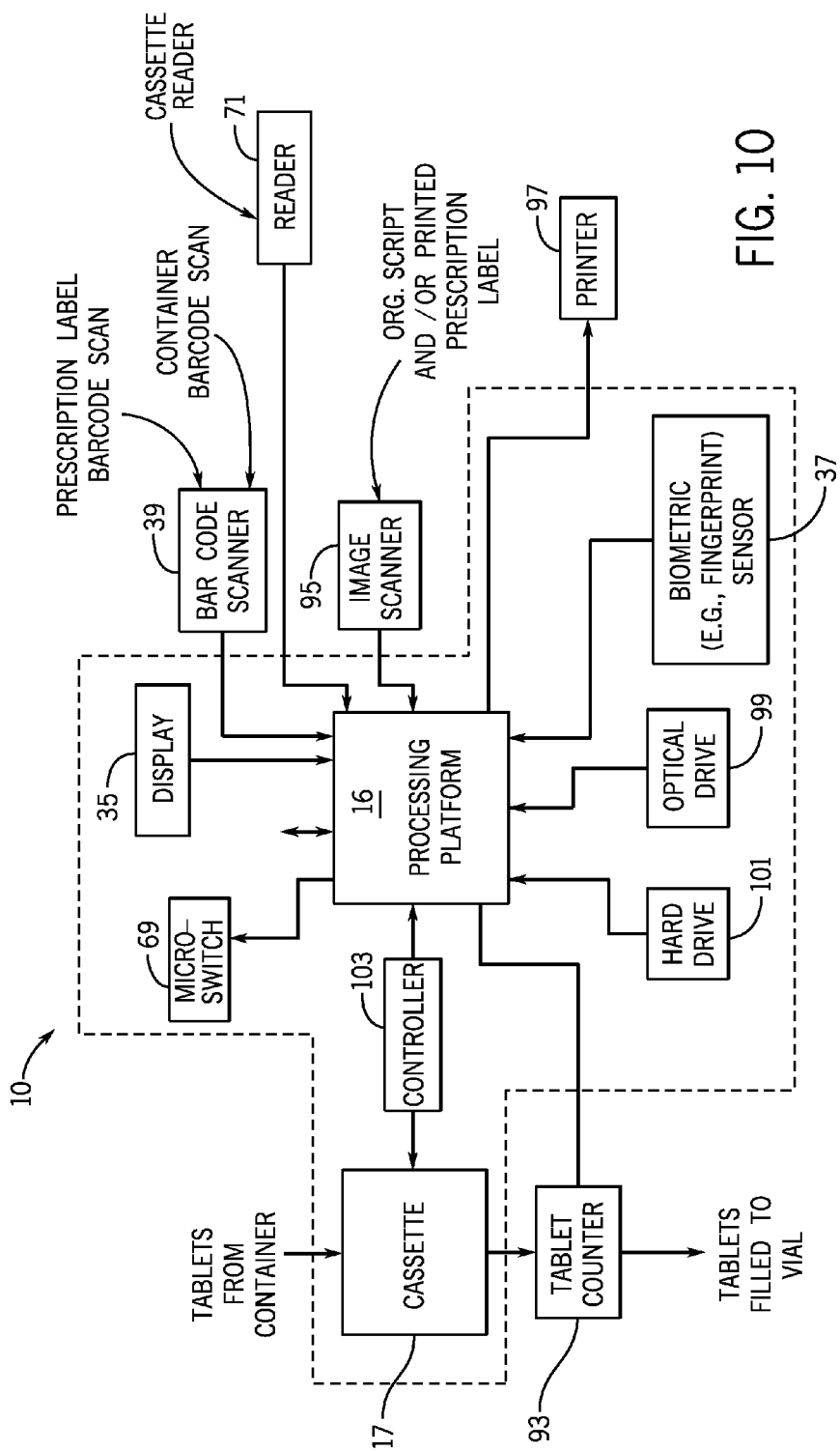
FIG. 10 is a schematic block diagram showing an exemplary data processing platform for use with the exemplary multi-cassette medicament dispensing machine of FIG. 1 together with other components.

Multi-cassette medicament dispensing machine 10 further includes dispensing stations 29A and 29B which, in the example, receive containers 31 into which medicaments may be automatically dispensed by multi-cassette medicament dispensing machine 10. In the example, the containers are vials, but medicament holders or containers of other types (e.g., bottles) can be implemented in other embodiments. Storage bin 30 is also included for holding empty containers 31, lids for containers 31 or other necessary supplies. Vial-type containers 31 are positioned and held in place by opposed gripping arms 33 for filling with medicament and labeling with prescription information. Multi-cassette medicament dispensing machine 10 includes an input device, such as a touch screen display 35, which provides control of multi-cassette medicament dispensing machine 10 by its operator through data processing platform 16 (FIG. 10). In other preferred embodiments, the input device may include a keyboard, mouse or other data input device for providing specific functions or controls to multi-cassette medicament dispensing machine 10.

During operation of multi-cassette medicament dispensing machine 10, it may be necessary for the user to be approved to initiate or complete certain functions. To verify that an individual machine operator has the credentials necessary to operate multi-cassette medicament dispensing machine 10, a biometric sensor 37 may be provided. Biometric sensor 37 may sense a user's fingerprint to identify the individual operator so that the logic can confirm the operator has the necessary credentials. Biometric sensor 37 may also provide for the user to input confirmatory information to data processing platform 16. Such verification and approval may be controlled by one or more of such sensor devices 37 and such devices may include other personal scanning controls such as retina scanners, palm readers, touch screen displays and the like.

Multi-cassette medicament dispensing machine 10 may also include a reading device for verifying codes on one or more cassettes 17, vial-type containers 31 or other containers during operation of multi-cassette medicament dispensing machine 10. In the exemplary embodiment of FIG. 1, the scanning device is illustrated as a bar code scanner 39. Bar code scanner 39 is held in place on multi-cassette medicament dispensing machine 10 by scanner support 41. It will be understood that any type of scanner and reader combination may be used including combinations such as RFID tag and RFID tag reader, QR code and QR code reader and the like.

Figure 3:
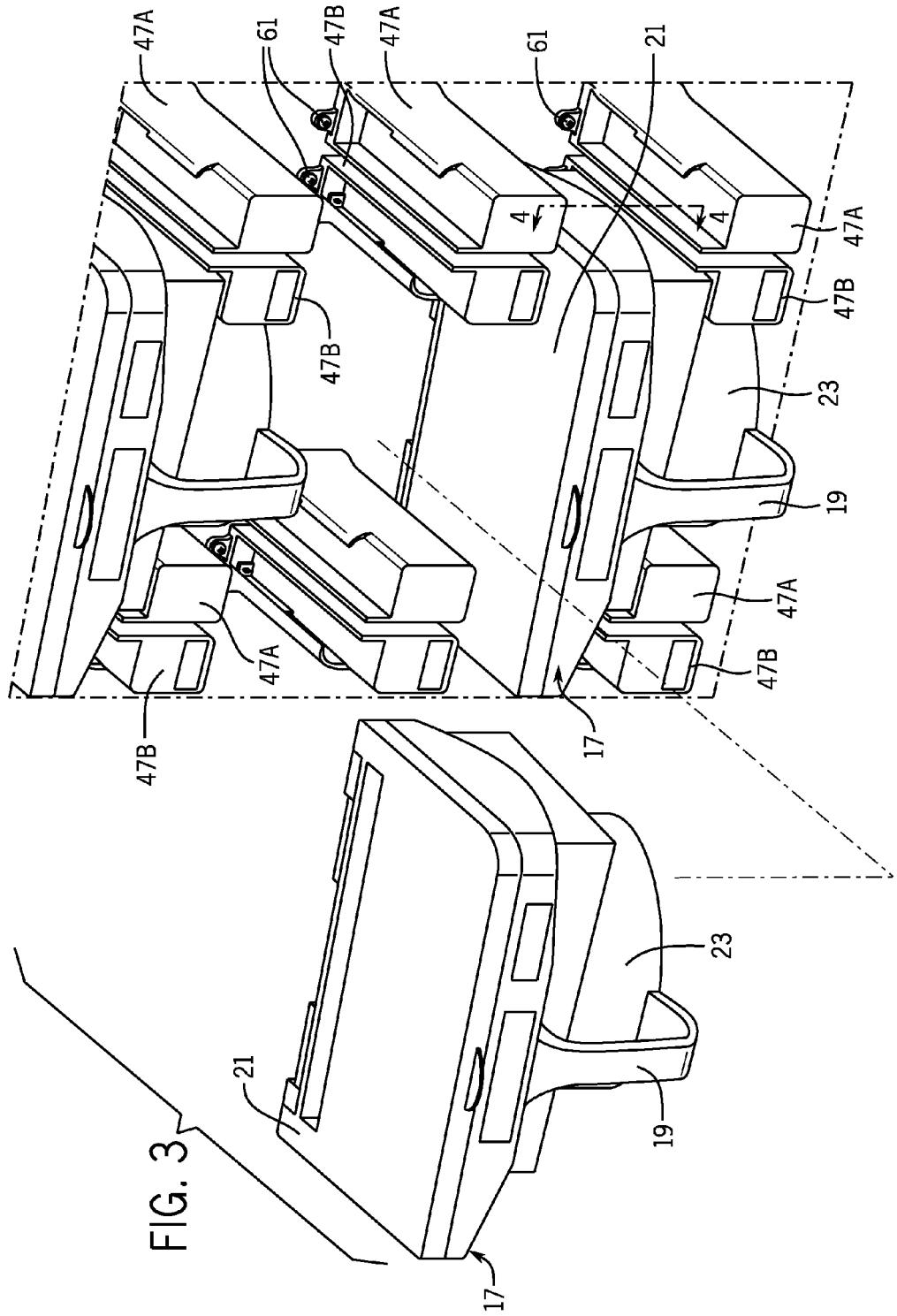
FIG. 3 is a perspective view of one of the cassettes of FIG. 2, but with the cassette removed from the multi-cassette medicament dispensing machine of FIG. 1.
Figure 4:
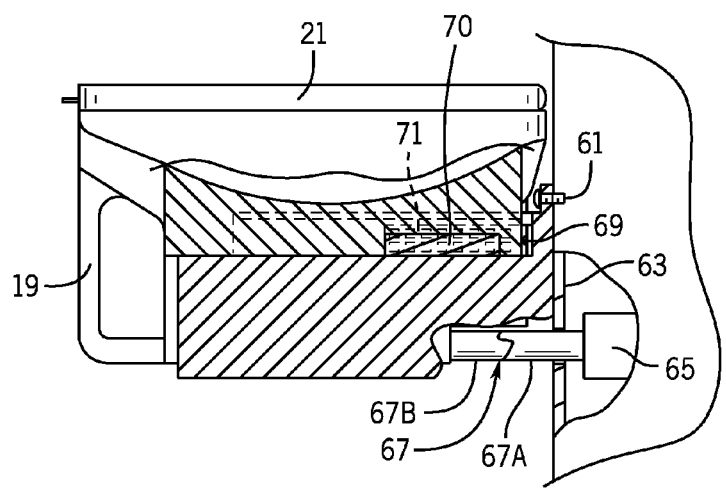
FIG. 4 is a section view of the cassette and mount taken along section 4-4 of FIG. 3.
Figure 5:
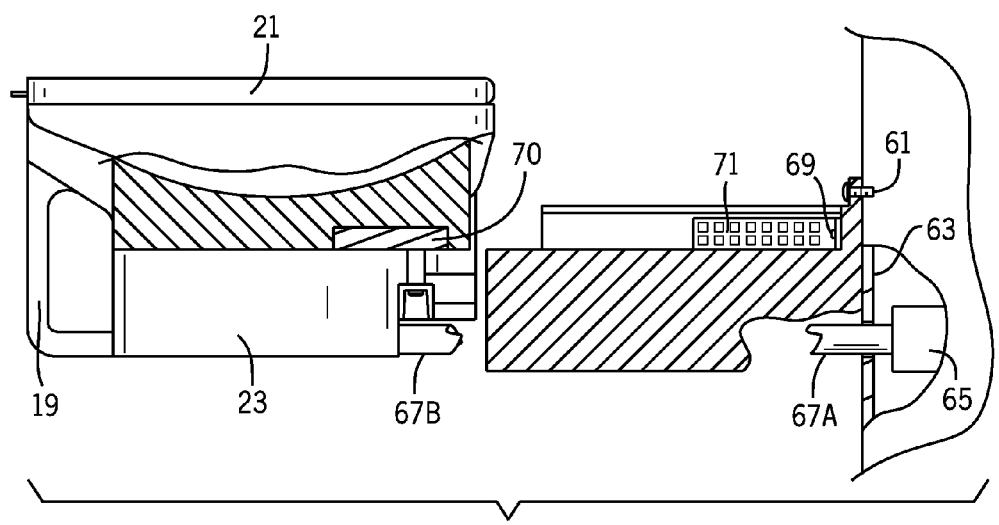
FIG. 5 is a section view of the cassette and mount of FIG. 4, but with the cassette removed from the multi-cassette medicament dispensing machine.

As can be seen in FIGS. 1-9, in operation, a cassette 17 is unmounted from multi-cassette medicament dispensing machine 10 and a signal is generated indicating the unmounted state of cassette 17. Cassette 17 may then be scanned with bar code scanner 39 or reader 71 (FIGS. 3-5). Upon initiating the scanning operation, input is provided to multi-cassette medicament dispensing machine 10 and to processing platform 16 as called for by multi-cassette medicament dispensing machine 10 operation to confirm that the expected cassette 17 with the expected medicament is present for replenishment. Such replenishment may take place at a replenishment station, such as replenishment station 43 or at another location as determined by the user.

Figure 7:
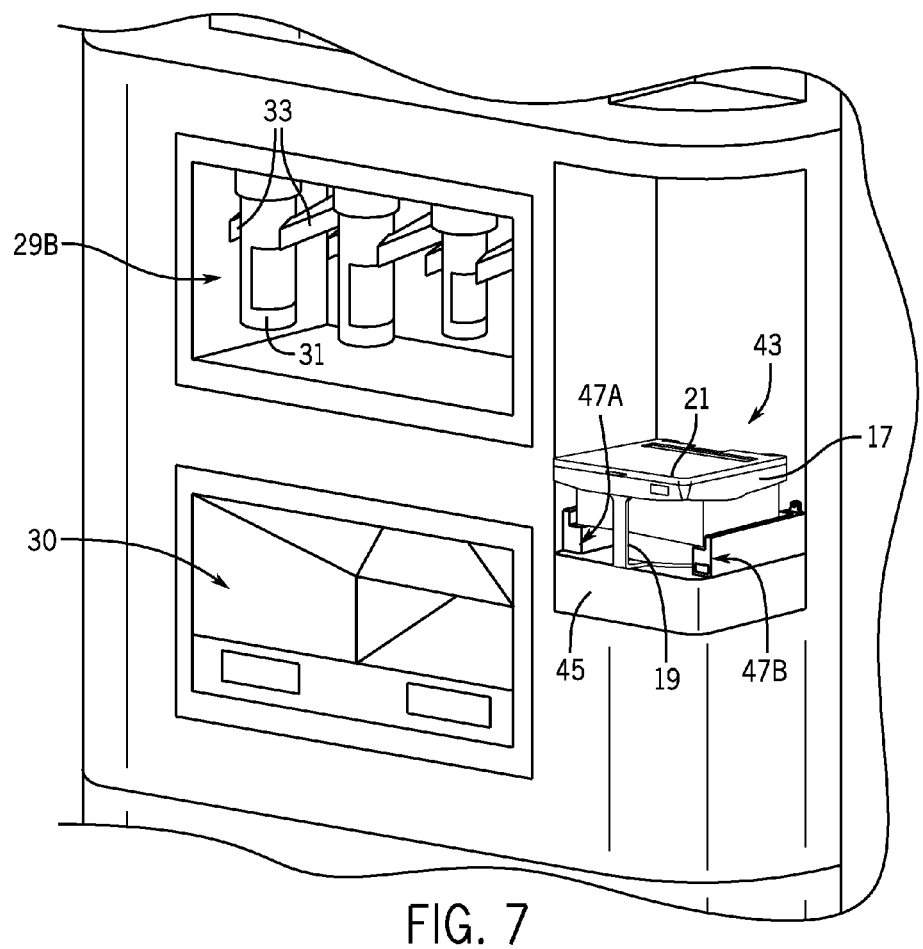
FIG. 7 is a partial perspective view of the multi-cassette medicament dispensing machine of FIG. 1, but showing an exemplary cassette installed in a replenishment station.
Figure 8:
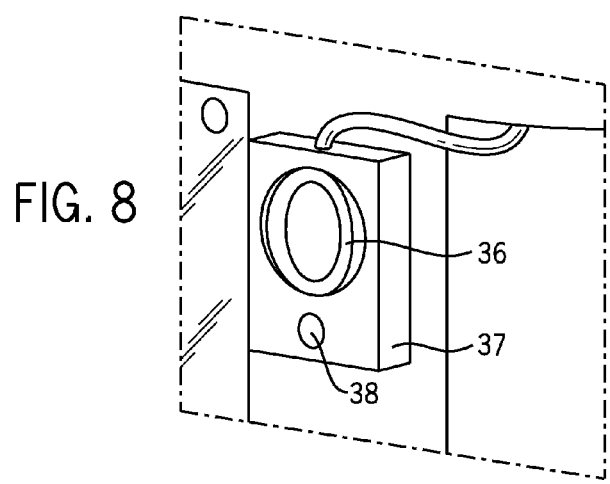
FIG. 8 is an exemplary biometric reader device taken along detail portion 8-8 of FIG. 1.
Figure 9:
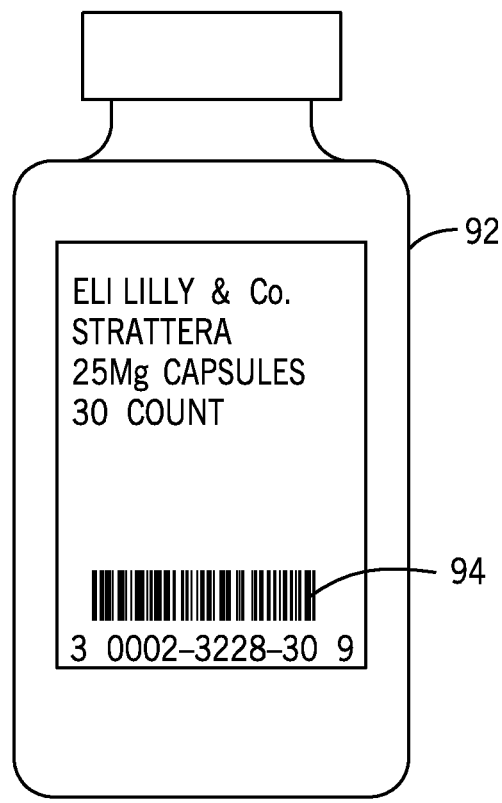
FIG. 9 is an exemplary medicament container holding tablet-form medicament.

In the example of FIG. 1, replenishment station 43 which may have a replenishment base 45 and opposed cassette mounts 47A and 47B into which cassette 17 may be placed (see FIG. 7). Bar code scanner 39 or reader 71 may be used to scan cassette 17 or a medicament container 92 with a bar code 94 (FIG. 9) including a medicament for replenishing cassette 17 or a container holding an unclaimed prescription with medicaments to be restocked into the cassette. Placement of cassette 17 into replenishment station 43 and engaging cassette 17 on cassette mounts 47A, 47B provides an indication that cassette 17 is ready for replenishment with a particular medicament as expected by multi-cassette medicament dispensing machine 10.

Multi-cassette medicament dispensing machine 10 also includes power switch 49 and power indicator 51. Upon actuation of power switch 49, power indicator 51 is illuminated and multi-cassette medicament dispensing machine 10 initiates a power on boot-up cycle. Multi-cassette medicament dispensing machine 10 may also include a label printer access panel 53 which allows access to the interior of multi-cassette medicament dispensing machine 10 to change the label printing stock (not shown) used for labeling vials 31 with prescription information upon filling. Access panel 53 may be opened and closed by means of handle 55. Access panel 53 may be secured by means of lock 57. Indicator 59 provides visual indication of the status of access panel 53.

During further operation of multi-cassette medicament dispensing machine 10, each cassette 17 may be rapidly coupled to, and decoupled from, cassette mounts 47A, 47B permitting a pharmacy to rapidly count and dispense different types of tablet-form medicaments from the appropriate cassette 17 (see FIGS. 2-5). Cassettes 17 may be used as an alternative to a container from the manufacturer, particularly for more frequently-used tablet-form products.

Use of cassette 17 is convenient and efficient, and a pharmacy may utilize any number of cassettes such as the group of cassettes 15 shown in FIG. 1. Each cassette 17 is loaded with one type of tablet-form medicament or other product. Typically, the most commonly dispensed medicaments are loaded in the group of cassettes 15 and are readily available for dispensing by multi-cassette medicament dispensing machine 10. In the example, each cassette 17 has a mating structure enabling any cassette 17 to be rapidly coupled to, and decoupled from any of the cassette mounts 47A, 47B. The mating structure of each cassette 17 can be identical, but can also be specific to a given location of cassette 17. Additional keying, pinning, connecting or similar identification of a given cassette 17 can also be included to provide confirmation that each cassette 17 is mounted at the proper location in multi-cassette medicament dispensing machine 10.

Each cassette 17 may be calibrated for a particular size and shape of tablet or may have a single design provided to accommodate only one tablet size or shape. When coupled to multi-cassette medicament dispensing machine 10 through cassette mounts 47A, 47B, cassette 17 is in position to feed tablets when called for by data processing platform 16. When not coupled to multi-cassette medicament dispensing machine 10 through cassette mounts 47A, 47B, each cassette 17 may be stored at a storage location (not shown) convenient to multi-cassette medicament dispensing machine 10.

Base 23 of cassette 17 may include a tactile material at its bottom, permitting cassette 17 to rest firmly on a bench or desktop surface (not shown). As further shown in FIGS. 1-7, cassette mounts 47A, 47B extend along base 23 when cassette 17 is mounted. Cassette mounts 47A, 47B may be secured to a wall 63 of multi-cassette medicament dispensing machine 10, for example by fasteners such as machine screws, an example of which are indicated by reference number 61.

A support 65 is attached within multi-cassette medicament dispensing machine 10 and provides the support for drive shaft 67 in the example. Drive shaft 67 transmits torque from a motor (not shown) to drive a platen which rotates within cassette base 23 when cassette 17 is mounted on cassette mounts 47A, 47B. To provide for installation of cassettes 17, shaft 67 may include two portions; shaft portion 67A supported by support 65 and shaft portion 67B on cassette 17. Other systems for powering operation of cassette 17 may be utilized (e.g., gears, belts, etc.).

Cassette 17, including handle 19, lid 21 and base 23, may be made of poly-carbonate or any suitable material having sufficient rigidity and strength. Cassette mounts 47A, 47B of the example are preferably fabricated of lightweight rectangular plastic tubing, but can be made of any other suitable material.

Figure 6:
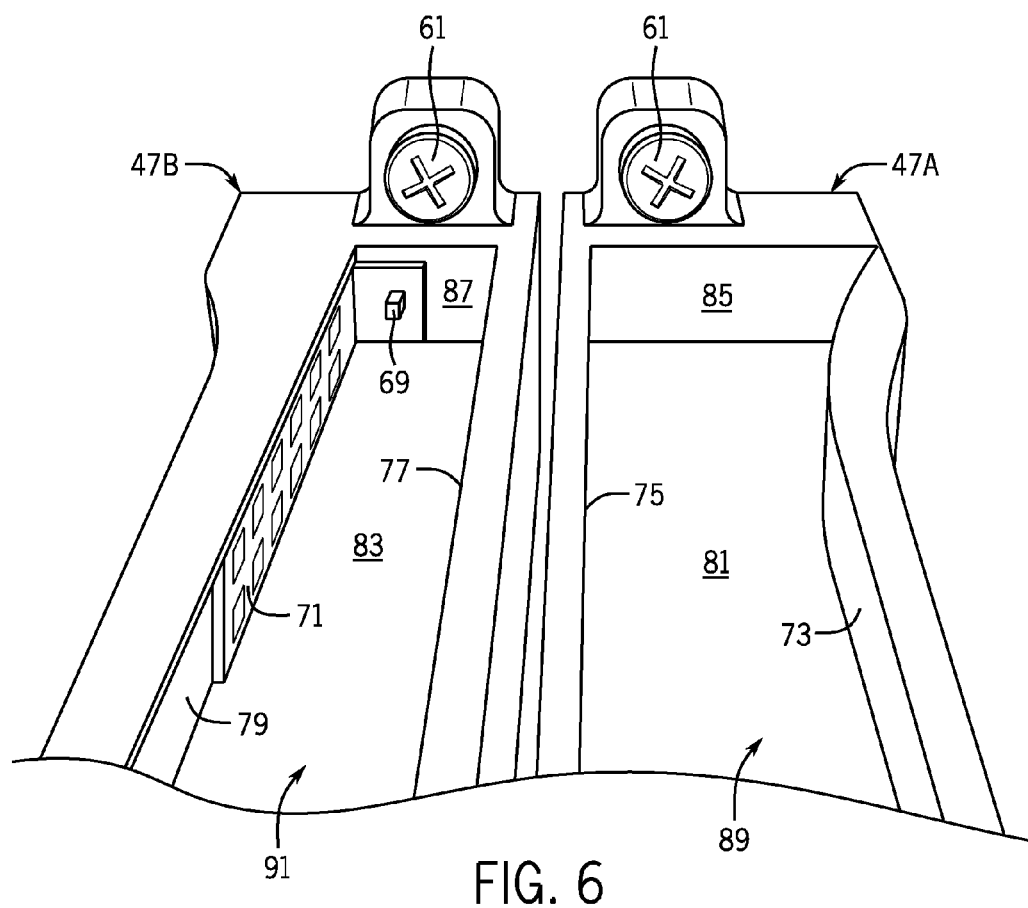
FIG. 6 is a perspective view of an exemplary cassette mount showing exemplary presence detection switching components.

In the exemplary embodiment illustrated, micro-switch 69 is positioned at the rear of cassette mount 47B. Micro-switch 69 is closed by movement of cassette 17 along cassette mounts 47A, 47B into contact with micro-switch 69 as is shown in FIGS. 4-6. Closure of micro-switch 69 indicates to multi-cassette medicament dispensing machine 10 that cassette 17 is fully mounted on multi-cassette medicament dispensing machine 10 and cassette 17 may be in place for dispensing the medicament therein, if certain other conditions detailed below are met.

To identify cassette 17, a reader 71 may be included which detects a barcode 70 on each cassette 17 when cassette 17 is fully mounted as illustrated in FIGS. 1-6. Reader 71 may be a binary optical sensor. Each cassette 17 may include barcode 70 on its sidewall which may be positioned in the path of reader 71 when cassette 17 is fully mounted on cassette mounts 47A, 47B. Barcode 70 may be detected by reader 71 and reader 71 then generates a signal uniquely identifying the cassette 17 from records stored in non-volatile memory in the cassette record database which may be stored on hard drive 101, read by optical drive 99 or otherwise provided to processing platform 16. Detection of bar code 70 by reader 71 in this manner enables multi-cassette medicament dispensing machine 10 to immediately identify the contents of any cassette 17 once mounted on mounts 47A, 47B. The combination of bar code 70 and reader 71 allows any cassette to be identified by multi-cassette medicament dispensing machine 10 at any cassette mounting location. This is desirable because any cassette 17 of the group of cassettes 15 is always identified by multi-cassette medicament dispensing machine 10. Any type of machine-readable code and reader combination may be used to identify cassette 17. Other such combinations may include RFID tags and RFID tag readers, QR codes and QR code readers and similar combinations.

As illustrated in FIGS. 1-6, cassette mounts 47A, 47B of the exemplary embodiment are formed as a pair of fixed-position elongate receivers. As is detailed in FIG. 6, each receiver includes a pair of spaced apart walls 73 (outer), 75 (inner) or 77 (inner), 79 (outer), a bottom wall 81, 83 and stop wall 85, 87 forming a female opening 89, 91 therebetween for snugly receiving a cassette 17 thereby supporting the cassette. Walls 73, 75, 77, 79, 81, 83, 85, 87 limit lateral and downward movement of cassette 17 when coupled to multi-cassette medicament dispensing machine 10. Cassette mounts 47A, 47B are "universal" mounts in that any cassette (e.g., cassette 17) may be installed and supported thereon.

The data processing platform 16 (FIG. 10) of multi-cassette medicament dispensing machine 10 carries out logical flow of signals which operate the multi-cassette medicament dispensing machine 10. Data processing platform 16 may include one or more printed circuit boards that include a microprocessor, non-volatile memory and interface circuitry thereon to interface with and control multi-cassette medicament dispensing machine 10 and the group of cassettes 15 during medicament fulfillment operations. These operations include control of pharmacy workflow involving fulfillment of prescriptions which require cassette verification and medicament counting including tablet, pills and the like.

A preferred embodiment of the relationship of the processing platform to the other modules of multi-cassette medicament dispensing machine 10 is depicted in the schematic block diagram of FIG. 10. Data processing platform 16 is electrically connected to a controller 103 which controls cassette 17 through shaft 67 connected to a motor (not shown). Display 35, biometric sensor 37, bar code scanner 39, reader 71, micro-switch 69 and an optional tablet counter 93 may also be connected electrically to processing platform 16. As shown in FIG. 10, additional modules including an image scanner 95, printer 97, optical drive 99, hard drive 101 and the like may also be electrically connected to data processing platform 16. It will be understood that one or more of the modules depicted may be included in one or more configurations in various embodiments of multi-cassette medicament dispensing machine 10 depending on the implementation desired by the user, pharmacy or dispensing location.

Figure 11:
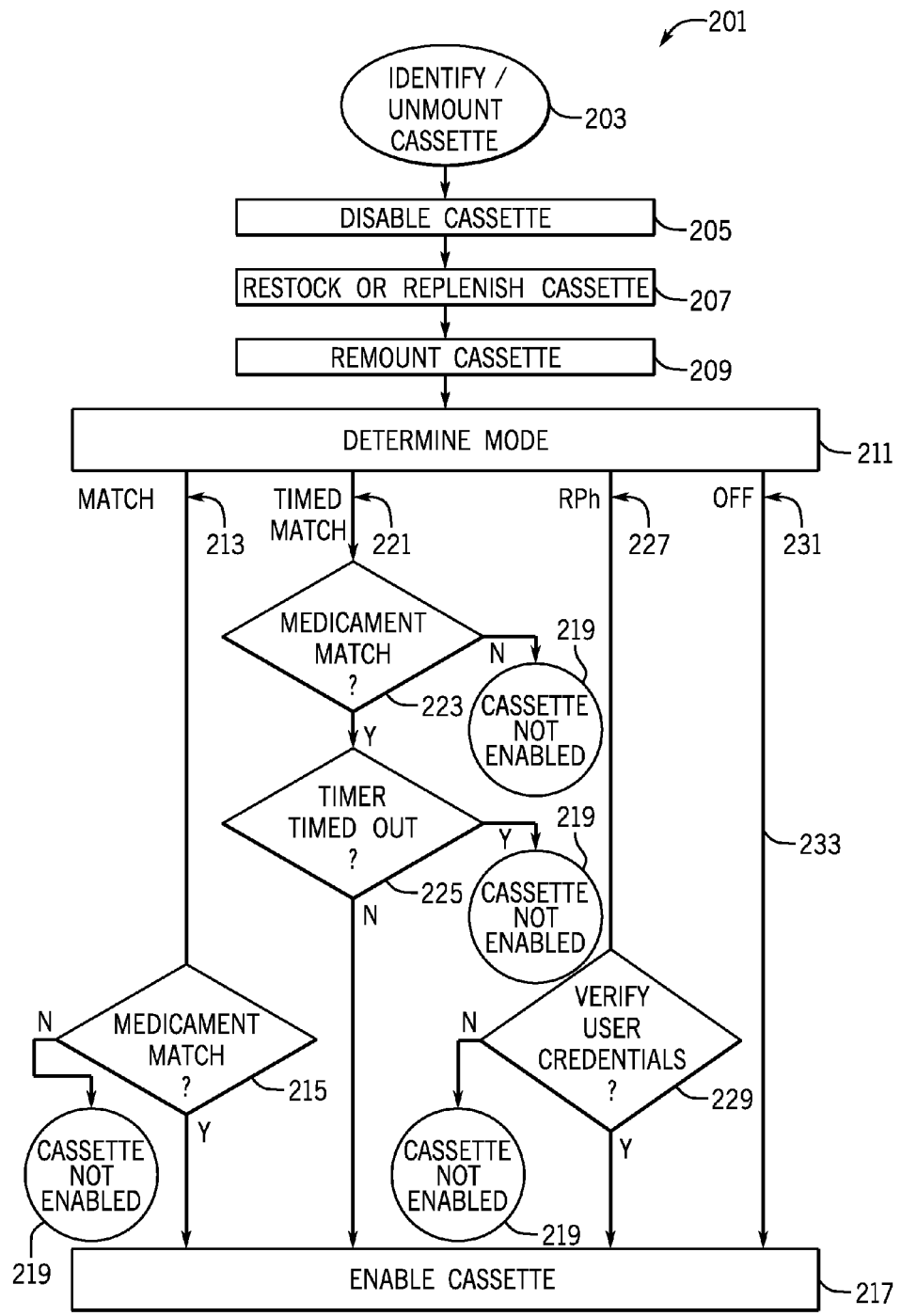
FIG. 11 is a logic flow diagram illustrating an embodiment of a method for controlling medicament dispensing from a cassette.

The logical signal flow of one preferred embodiment of the method which includes desirable features to prevent improper loading, improper verification, contamination or other errors in returning medicaments to stock and refilling medicaments in multi-cassette medicament dispensing machine 10 is depicted in FIG. 11. As can be seen in FIG. 11, certain method steps which are executed by instructions in non-volatile memory of data processing platform 16 occur in an embodiment 201 when cassette 17 is identified by or is unmounted from multi-cassette medicament dispensing machine 10 at decision point 203, and controller 103 (see FIG. 10) simultaneously receives a request to dispense medicament from cassette 17 to fulfill a prescription order. Display 35 may also display data relating to cassette 17, medicament supply container such as medicament container 92 (FIG. 9) when cassette 17 is replenished from medicament supply container 92, or vial 31 in the situation when a prescription is returned-to-stock in cassette 17, all as described herein. In addition, display 35 may display any of the data required to identify a cassette to the system, make decisions at the various decision points, method steps and the like as also described herein.

FIG. 11 illustrates exemplary logic and signal flow for a single cassette. Such logic and signal flow is carried out by controller 103 to operate each cassette 17 of the plurality of cassettes 15. In the exemplary embodiment of FIGS. 10 and 11, controller 103 is set to poll the group of cassettes in multi-cassette medicament dispensing machine 10 approximately five times per second, or every 200 milliseconds (ms). As part of the response back from controller 103, the state of all cassettes 17 of cassette group 15 of multi-cassette medicament dispensing machine 10 are received every 200 ms. It should be understood that any appropriate time interval may be used to poll multi-cassette medicament dispensing machine 10 depending on the particular combination of hardware, software and logic used in a specific embodiment. It should also be understood that 200 ms is merely a design choice for the exemplary embodiment illustrated.

The response provided back to controller 103 may be a signal indicating that cassette 17 is missing or not installed in multi-cassette medicament dispensing machine 10, that cassette 17 is installed in multi-cassette medicament dispensing machine 10 and is ready for operation and to dispense medicament, or that cassette 17 was previously unmounted and even though cassette 17 is in position in multi-cassette medicament dispensing machine 10, cassette 17 needs resetting to be operational to dispense medicament. As stated above, the logic and signal flow for one cassette 17 is the same logic and signal flow that is performed for management of the plurality of the cassettes 15 in multi-cassette medicament dispensing machine 10 of FIG. 1.

The flow diagram of FIG. 11 includes diamond-shaped elements which represent method steps which are decision points each having "Yes" or "No" responses labeled "Y" and "N," respectively. For further convenience and brevity, these decision points have not been labeled with reference numbers. However, in the text, these responses will be referred to using the reference number of the corresponding decision point followed by a "Y" or an "N" as appropriate.

As described above, cassette 17 may be identified by multi-cassette medicament dispensing machine 10 when it is mounted on multi-cassette medicament dispensing machine 10. A first signal is generated indicating that cassette 17 is fully mounted and micro-switch 69 is closed. Cassette 17 is then enabled for operation in response to the first signal. Referring to FIG. 11, cassette 17 may be unmounted from multi-cassette medicament dispensing machine 10 and a second signal generated at decision point 203. Upon unmounting at decision point 203, cassette 17 is disabled from further operation at decision point 205 in response to the second signal. At decision point 207, lid 21 of cassette 17 may be opened to permit replenishing of cassette 17 with medicament from a supply such as container 92, or medicament from a previously dispensed prescription order may be returned to stock in cassette 17. Further, after unmounting cassette 17 at least partially from the mount, the lid 21 may be opened when cassette 17 is at least partially unmounted to permit medicaments to be loaded into cassette 17.

After cassette 17 has been replenished or a return-to-stock process has been completed at decision point 207, cassette 17 may be remounted in multi-cassette medicament dispensing machine 10. Upon remounting cassette 17 in multi-cassette medicament dispensing machine 10, a dispense request may be received and controller 103 may then determine whether the cassette is fully mounted at decision point 209 and micro-switch 69 is closed. If the cassette is not fully mounted, indicated by micro-switch 69 being open, no further logic flow is required since the cassette is not available for either dispensing or further logical determinations to be made. At this point, the operator can again unmount cassette 17 at decision point 203 and begin the procedure over again, if desired.

If cassette 17 is fully mounted, then micro-switch 69 is engaged and it is determined at decision point 209 whether or not cassette 17 has been enabled (authorized to dispense medicament). In embodiment 201, the state of each cassette 17 (enabled or disabled) is set and stored as certain events occur. Referring to FIG. 11, additional logic flow of embodiment 201 illustrates method steps which occur when cassette 17 is fully mounted, as indicated by the first signal when micro-switch 69 is closed, as described above. Decision point 209 corresponds to the first signal being received by data processing platform 16 through controller 103 from micro-switch 69 sensing the fully mounted state of cassette 17.

FIG. 11 also illustrates how embodiment 201 of the inventive method may further respond upon sensing the fully mounted state of cassette 17. In controlling the return-to-stock of a medicament from previously processed but unclaimed prescriptions or controlling the replenishment of cassette 17 from a supply of a particular medicament in embodiment 201, the label of an unclaimed prescription or the label of a medicament supply container (such as container 92) may be scanned. When such scanning occurs, the system retrieves all of the details of the prescription or supply including medicament identity, tablet size, lot number, and count and stores the return-to-stock or replenishment transaction in the database. During a return-to-stock or replenishment transaction, cassette 17 is temporarily unmounted from its mount 47A, 47B at decision point 203 to permit return-to-stock or replenishment of the medicament into cassette 17. Multi-cassette medicament dispensing machine 10 records the event of that return-to-stock or replenishment transaction (sets the return-to-stock or replenishment state) and sets the authorization state of cassette 17 before removal. If cassette 17 is unmounted from its mount 47A, 47B in multi-cassette medicament dispensing machine 10, cassette 17 will be disabled at decision point 205 and the second signal is generated. Cassette 17 will remain disabled until cassette 17 is remounted at decision point 209. At decision point 209, cassette 17 may be enabled for further operation upon generation of a first signal and a third signal as described below.

When cassette 17 is unmounted from multi-cassette medicament dispensing machine 10 and a return-to-stock or replenishment transaction has been initiated, one of several modes can be determined at decision point 211. In a first mode following branch 213 ("MATCH"), the scanning of cassette 17 generates a fourth signal and scanning of the unclaimed prescription vial such as vial 31, or the medicament supply container 92 generates a fifth signal. The fourth and fifth signals are compared and if there is a match, a sixth signal is generated indicating there is a match of the scan of cassette 17 and the scan of vial 31 or supply container 92. Confirmation of a match of the scans indicating a medicament match can be obtained through branch 213 ("MATCH") at decision point 215Y. Confirmation of a match by comparing such scans ensures that unclaimed medicaments from a pharmacy will-call holding area are poured back into the proper cassette 17 and that medicaments which may look alike from a supply container are not inadvertently poured into the wrong cassette 17. If such confirmation is obtained from the scans, then the return-to-stock or replenishment transaction can proceed and cassette 17 can be returned to multi-cassette medicament dispensing machine 10. Upon return, cassette 17 will be enabled for further use in multi-cassette medicament dispensing machine 10 at decision point 217. If the medicament to be returned-to-stock or filled from a medicament supply container 92 does not match the medicament in cassette 17 at decision point 215N, the system then enters a "cassette not enabled" state at 219, waiting for the next command. An alert may also be initiated by multi-cassette medicament dispensing machine 10 to indicate the mismatched state. Such alert may be an audio alert or an alert provided on display 35.

In a second mode, after cassette 17 is unmounted, a return-to-stock or replenishment timer, set to a preset return-to-stock or replenishment interval, is started after the second signal is generated as described above, through branch 221 ("TIMED MATCH") from decision point 211. In this mode, the pharmacist or pharmacy technician is provided a set time interval to pour the medicament of the unclaimed prescription container such as vial 31 or medicament from a refill supply container 92 into cassette 17 and fully remount cassette 17. The timed match mode forces the pharmacist or the technician to promptly complete restock or replenishment of cassette 17 so errors are avoided and medicament does not become dirty or otherwise contaminated.

When cassette 17 is remounted at decision point 209, the system knows that timed match is occurring, determined from the mode at decision point 211, and indicated by a medicament match at decision point 223Y. At decision point 225, it is then determined whether the user has remounted cassette 17 within the allowed return-to-stock or replenishment time interval, indicated by whether or not the return-to-stock or replenishment timer has timed out. If the medicament does not match (decision point 223N) or return-to-stock timer or replenishment has timed out (decision point 225Y), the system then enters a "cassette not enabled" state at 219, waiting for the next command to be initiated. An alert may also be initiated to indicate the not enabled state as previously described.

If it is determined at decision point 225 that the return-to-stock or replenishment timer has not timed out (decision point 225N), indicating that the user was able to remount cassette 17 within the allotted time interval, cassette 17 is enabled at decision point 217. Subsequently, the system is again ready to detect an unmounting of cassette 17, a dispense request or a change in authorization state. It may be appreciated that the return-to-stock or replenishment time interval may start when cassette 17 is unmounted from multi-cassette medicament dispensing machine 10 or may start when cassette 17 is unmounted from a replenishment station such as replenishment station 43. It will also be appreciated that the return-to-stock or replenishment time interval may be any required time interval, including any settable time interval or any combination of time intervals, determined by the particular use of multi-cassette medicament dispensing machine 10.

At decision point 211, if it is determined that a heighten review is needed before cassette 17 is remounted, a verified user, typically a registered pharmacist, needs to provide proper credentials to operate multi-cassette medicament dispensing machine 10. In such mode, branch 227 ("RPh") is followed. Through branch 227, the registered pharmacist (RPh) mode is engaged and the system is allowed to continue operation at decision point 229 until cassette 17 is again unmounted. When cassette 17 is unmounted, the system stores its previous authorization state. In the RPh mode, every transaction must be verified for cassette 17 to be enabled at decision point 217. The RPh mode allows anyone to replenish a medicament or return a medicament to stock in cassette 17, but each transaction has to be verified as correct by an authorized user of multi-cassette medicament dispensing machine 10 at decision point 229. The benefit of the RPh mode is maintaining accountability by creating a record of who verified or signed off on each transaction.

In the RPh mode, there is a biometric read by biometric reader 37 of a finger print of the registered pharmacist who verified each transaction. After the registered pharmacist verifies the transaction in the RPh mode at decision point 229, the third signal is generated and cassette 17 is enabled at 217. If the user's credentials cannot be verified at 229N, the system then enters a "cassette not enabled" state at 219, waiting for the next command to be initiated. An alert may also be initiated to indicate the not enabled state as previously described.

It will be appreciated that, while the RPh mode is shown as a separate path in the system illustrated in the exemplary embodiment of FIG. 11, such registered pharmacist verification can be implemented at any point in the flow path. Such points may be, for example, prior to the restock or replenishment of cassette 17 at decision point 207, after the cassette is remounted at decision point 209, or prior to or after determining the mode at decision point 211. Accordingly, decision point 209 can be placed at any decision point in the flow diagram at which registered pharmacist verification may be required prior to moving to the next decision point. This, of course, may be at multiple and/or simultaneous decision points in the flow diagram of FIG. 11. If the user's credentials cannot be verified at any decision point requiring verification, the system then enters a "cassette not enabled" state at 219, waiting for the next command to be initiated. An alert may also be initiated any time after a user's credentials cannot be verified, indicating the not enabled state as previously described.

In another mode of operation of multi-cassette medicament dispensing machine 10, it may be desirable to disable the mode determining function as shown in following branch 231 ("OFF") from decision point 211. In such case, path 233 eliminates the requirement of a medicament match at decision point 215 or 223, eliminates the need for the use of a timer at decision point 225 and eliminates the need for verification by a registered use of multi-cassette medicament dispensing machine 10 at decision point 229. In this "OFF" mode, multi-cassette medicament dispensing machine 10 can be used by any user without further qualification when cassette 17 is fully mounted for use and micro-switch 69 is closed in multi-cassette medicament dispensing machine 10. In the "OFF" mode multi-cassette medicament dispensing machine 10 may be operated without requiring a match, timed match or registered pharmacist verification as described above.

As can be seen from the exemplary embodiment of FIGS. 1-9, exemplary schematic block diagram of FIG. 10 and exemplary flow diagram of FIG. 11, a method for controlling medicament dispensing from cassette 17 moved from mounts 47A, 47B in multi-cassette medicament dispensing machine 10 is provided. When a loaded cassette 17 is fully on mounts 47A, 47B and micro-switch 69 is closed and, if necessary, cassette 17 is verified, a first signal is generated at decision point 209 which enables operation of cassette 17. When cassette 17 is at least partially unmounted from mounts 47A, 47B and micro-switch 69 is opened, a second signal is generated at decision point 205 which indicates that cassette 17 has been unmounted. Upon generating the second signal at decision point 205, the operation of multi-cassette medicament dispensing machine 10 is disabled, even if cassette 17 is fully remounted into position on mounts 47A and 47B and switch 69 is closed for operation of multi-cassette medicament dispensing machine 10.

Operation in this manner prevents unauthorized refills or return to stock transactions from occurring in multi-cassette medicament dispensing machine 10.

In another exemplary embodiment, after operation of multi-cassette medicament dispensing machine 10 is disabled through the removal of cassette 17 and opening of micro-switch 69 (generating the second signal at decision point 205), a third signal may be generated at decision point 217. Generation of the third signal at decision point 217 indicates that cassette 17 has determined a mode at decision point 211 and is ready for further dispensing of medicaments when cassette 17 is fully mounted on mounts 47A, 47B, switch 69 is again closed and cassette 17 is enabled. The mode determining operation at decision point 211 requires that one of the paths 213, 221, 227 or 231 in the flow diagram of FIG. 11 be followed for further operation of multi-cassette medicament dispensing machine 10.

In another exemplary embodiment, a medicament match may be confirmed between a cassette 17 and a medicament supply container, such as medicament container 92. A fourth signal may be generated identifying cassette 17 which is compared with a fifth signal identifying the medicament in container 92. Such signals can be generated as described above through scanning of bar codes and the like. If the medicament in the cassette 17 matches the medicament in container 92 a sixth signal may be generated indicating a match between cassette 17 and medicament supply container 92 thereafter enabling further operation of cassette 17.

Many of the functional units described in this specification have been labeled as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, other discrete components or any combination of such elements. A module may also be implemented in programmable hardware devices such as field programmable gate arrays, programmable array logic, programmable logic devices or the like.

One skilled in the art will recognize, however, that the disclosure may be practiced without one or more of the specific details, or with other methods, components, materials, and the like. In other instances, well-known structures, materials, or operations are not shown or described in detail to avoid obscuring aspects of the disclosure.

Reference throughout this specification to "the embodiment," "this embodiment," "the previous embodiment," "one embodiment," "an embodiment," "a preferred embodiment" "another preferred embodiment," "an exemplary embodiment," "example," or similar language means that a particular feature, structure, or characteristic described in connection with the embodiment is included in at least one embodiment. Thus, appearances of the phrases "in the embodiment," "in this embodiment," "in the previous embodiment," "in one embodiment," "in an embodiment," "in a preferred embodiment," "in another preferred embodiment," "in an exemplary embodiment," "in the exemplary embodiment," "in an example," "in the example" and similar language throughout this specification may, but do not necessarily, all refer to the same embodiment.

Furthermore, the described features, advantages, and characteristics of the disclosure may be combined in any suitable manner in one or more embodiments. One skilled in the relevant art will recognize that the disclosure may be practiced without one or more of the specific features or advantages of a particular embodiment. In other instances, additional features and advantages may be recognized in certain embodiments that may not be present in all embodiments.

While the present disclosure has been described in connection with certain exemplary or specific embodiments, it should be understood that the disclosure is not limited to the disclosed embodiments, but, on the contrary, is intended to cover various modifications, alternatives, modifications and equivalent arrangements as will be apparent to those skilled in the art. Any such changes, modifications, alternatives, modifications, equivalents and the like may be made without departing from the spirit and scope of the disclosure.

What is claimed is:

1. A method for controlling medicament dispensing from a cassette moved from a mount for the cassette, the method comprising:
   mounting the cassette fully on the mount, the cassette being loaded with bulk-form medicaments;
   identifying the mounted cassette;
   generating a first signal indicating that the cassette is both identified and fully mounted;
   enabling operation of the cassette responsive to the first signal;
   unmounting the cassette at least partially from the mount;
   generating a second signal indicating that the cassette has been at least partially unmounted;
   executing instructions responsive to the second signal disabling further operation of the cassette even if the cassette is both fully remounted and identified;
   generating a third signal indicating that the cassette is verified as containing medicament which is correct and is ready for further dispensing of medicaments;
   remounting the cassette fully on the mount before or after generating the third signal;
   generating the first signal indicating that the cassette is fully remounted; and
   executing instructions responsive to the first and third signals enabling further operation of the cassette.

2. The method of claim 1 wherein generating the first signal includes contacting a switch with the cassette when the cassette is fully mounted.

3. The method of claim 2 wherein generating the second signal includes spacing the cassette from the switch when the cassette is at least partially unmounted.

4. The method of claim 1 further comprising, after executing the instructions responsive to the first and third signals enabling further operation of the cassette, dispensing medicaments from the cassette.

5. The method of claim 4 wherein dispensing medicaments from the cassette includes dispensing all of the medicaments from the cassette.

6. The method of claim 4 further comprising, after unmounting the cassette at least partially from the mount, loading further bulk-form medicaments into the cassette.

7. The method of claim 6 wherein the cassette includes a lid and the method further comprises, after unmounting the cassette at least partially from the mount and before loading further bulk-form medicaments into the cassette:
   allowing the lid to open when the cassette is at least partially unmounted; and
   opening the lid permitting the medicaments to be loaded into the cassette.

8. The method of claim 6 further comprising, before or after loading further bulk-form medicaments into the cassette, verifying that the cassette was correctly loaded with the medicaments.

9. The method of claim 8 wherein generating the third signal includes triggering the third signal with a user-input device.

10. The method of claim 9 wherein triggering the third signal with the user-input device includes placing a finger against a fingerprint reader user-input device.

11. The method of claim 9 wherein triggering the third signal with the user-input device includes placing a finger against a touch screen video display user-input device.

12. The method of claim 9 wherein triggering the third signal with the user-input device includes reading a code associated with the cassette with a code reader user-input device.

13. The method of claim 1 wherein generating the second signal includes starting a timer with a time interval and enabling further operation of the cassette must occur before expiration of the time interval.

14. The method of claim 13 further comprising starting the timer after generating the second signal before remounting the cassette fully on the mount.

15. The method of claim 1 further comprising generating a fourth signal identifying the cassette, a fifth signal identifying a container holding a medicament for pouring into the cassette and a sixth signal identifying a match of the cassette and the container holding a medicament before enabling further operation of the cassette.

16. The method of claim 15 wherein the container holding a medicament holds an unclaimed prescription with medicaments to be restocked into the cassette.

17. The method of claim 15 wherein the container holding a medicament is a supply container which holds a quantity of medicaments to replenish the cassette.

18. A method for controlling medicament dispensing from a reloadable cassette to prevent unauthorized operation of the cassette following replenishment, the method comprising:
   mounting the cassette fully on a mount, the cassette being loaded with bulk-form medicaments;
   identifying the mounted cassette;
   generating a first signal indicating that the cassette is both identified and fully mounted;
   enabling operation of the cassette responsive to the first signal;
   dispensing medicaments from the cassette;
   unmounting the cassette at least partially from the mount;
   generating a second signal indicating that the cassette has been at least partially unmounted; and
   executing instructions responsive to the second signal disabling operation of the cassette even if the cassette is both fully remounted and identified, thereby preventing any unauthorized operation of the cassette should the cassette have been replenished after the at least partial unmounting.

19. The method of claim 18 further comprising, after executing the instructions disabling operation of the cassette:
   generating a third signal indicating that the cassette is verified as containing medicament which is correct and is authorized and ready for further dispensing of medicaments;
   remounting the cassette fully on the mount before or after generating the third signal;
   generating the first signal indicating that the cassette is fully remounted; and
   executing instructions responsive to the first and third signals enabling further operation of the cassette.

20. The method of claim 19 wherein generating the first signal includes contacting a switch with the cassette when the cassette is fully mounted.

21. The method of claim 20 wherein generating the second signal includes spacing the cassette from the switch when the cassette is at least partially unmounted.

22. The method of claim 21 further comprising, after executing the instructions responsive to the first and third signals enabling further operation of the cassette, dispensing medicaments from the cassette.

23. The method of claim 22 further comprising, after unmounting the cassette at least partially from the mount, loading further bulk-form medicaments into the cassette.

24. The method of claim 23 further comprising, before or after loading further bulk-form medicaments into the cassette, verifying that the cassette was correctly loaded with the medicaments.

25. The method of claim 24 wherein generating the third signal includes triggering the third signal with a user-input device.

* * * * *